(12) United States Patent
Komoschinski et al.

(10) Patent No.: US 6,433,228 B1
(45) Date of Patent: Aug. 13, 2002

(54) PROCESS FOR PREPARING 2-HALOGENATED INDAN-1-ONES

(75) Inventors: Joachim Komoschinski, Köln; Helmut Fiege, Leverkusen; Guido Steffan, Odenthal; Klaus-Christian Paetz, Burscheid, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/486,010

(22) PCT Filed: Aug. 13, 1998

(86) PCT No.: PCT/EP98/05141

§ 371 (c)(1),
(2), (4) Date: Feb. 18, 2000

(87) PCT Pub. No.: WO99/10306

PCT Pub. Date: Mar. 4, 1999

(30) Foreign Application Priority Data

Aug. 25, 1997 (DE) .......................................... 197 36 922

(51) Int. Cl.[7] ...................... C07C 49/697; C07C 45/46; C07C 245/20
(52) U.S. Cl. ...................................................... 568/319
(58) Field of Search ........................................ 568/319

(56) References Cited

U.S. PATENT DOCUMENTS 4,174,397 A  * 11/1979  Knabe et al. ................ 424/270

OTHER PUBLICATIONS

Gavina, Francisco; Costero, Ana M.; Gonzalez, Ana M.; Luis, Santiago V., J. Org. Chem. (1987), 52(14), 2997–9.*
Rondestvedt, C.S. Jr., Organic Reactions, vol. 24, 1976, John–Wiley, New York, pp. 225–259.*
Johnson, W.S., Organic Reactions, vol. 2, 1944, John–Wiley, New York, pp. 114–177.*
John D. Roberts and Marjorie C. Caserio, "Basic Principles of Organic Chemistry", Benjamin, New York, 1964, pp. 257–259.*
Aldrich Chemical Company, Milwaukee, WI, 1992, p. 52.*
"Webster's New World Dictionary of the American Language, College Edition", Guralnik and Friend, Ed., World Publishing, Cleveland, 1962, p. 4.*

* cited by examiner

Primary Examiner—Richard L. Raymond
Assistant Examiner—Thomas C McKenzie
(74) Attorney, Agent, or Firm—Joseph C. Gil; Diderico van Eyl

(57) ABSTRACT

2-Halogenoindan-1-ones are prepared in an advantageous manner by converting anilines into diazonium salts and these, with acrylic compounds, into 3-phenyl-1-halogenoproprionic acid derivatives, and latter are cyclized.

5 Claims, No Drawings

PROCESS FOR PREPARING 2-HALOGENATED INDAN-1-ONES

This application is the National Stage Application of PCT/EP98/05141, which claims a priority from German Application 197 36 922.7 filed Aug. 25, 1997.

BACKGROUND OF THE INVENTION

The present invention relates to an improved process for preparing 2-halogenoindan-1-ones.

It is already known that, starting from 1-indan-1-ones, indanones which are halogenated in the α position to the keto group can be prepared by halogenation with elemental chlorine or bromine. This, however, requires the prior synthesis of the corresponding indanone system. This is difficult, in particular if the aromatic moiety of the molecule contains deactivating substituents such as, for example, $NO_2$, Cl, Br, acetyl, etc. It is only then possible to carry out the halogenation (see, for example, J. Org. Chem. 24, 843 (1959) and DE-A 26 40 358). These halogenations are not particularly selective, since they also give rise to polyhalogenated derivatives which then have to be removed in a complicated manner.

Indan-1-ones themselves can be prepared by Friedel-Crafts reactions from the corresponding dihydrocinnamic acids (see, for example, Organ. React., Volume II, Chapter 4). Such cinnamic acids are difficult to obtain, in particular when they contain, for example, halogeno or trifluoromethyl substituents. Particularly disadvantageous are the fact that the aldehyde precursors are sometimes to difficult to obtain, the low yields and the separate halogenation step.

The route for preparing 5-chloroindan-1-ones starting from 3-chloro-1-(4-chlorophenyl)-1-propanone is described in Bull. Soc. Chim. (1973), 11, 3096. Here, however, great amounts of an aluminium trichloride/sodium chloride mixture and high temperatures of, for example, 180° C. are required to achieve cyclization. According to WO 96/20151, the same starting material is cyclized using concentrated sulphuric acid; however, this requires highly diluted solutions to be used, which renders work-up difficult and is therefore rather uneconomical. Both processes only yield 5-chloroindan-1-ones which, in order to obtain 2-halogenoindan-1-ones, have to be further halogenated in a subsequent step.

DESCRIPTION OF THE INVENTION

A process for preparing 2-halogenoindan-1-ones of the formula

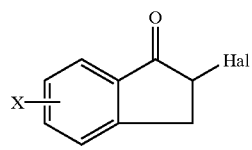

(I)

in which
X represents hydrogen, fluorine, chlorine, bromine, methyl, trifluoromethyl or methoxy and
Hal represents chlorine or bromine
has now been found which is characterized in that an aniline of the formula

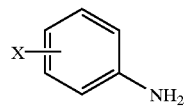

(II)

in which
X is as defined under formula (I)
is converted into the corresponding diazonium salt of the formula (III)

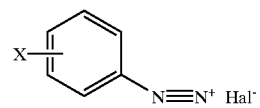

(III)

in which
X and Hal are as defined under formula (I),
this salt is reacted with an acrylic compound of the formula (IV)

(IV)

in which
Y represents COR where R=OH, Cl, Br, $OC_1$–$C_4$-alkyl or CN,
thus giving a compound of the formula (V)

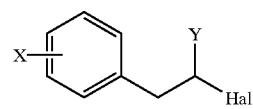

(V)

in which
X and Hal are as defined under formula (I) and
Y is as defined under formula (IV),
compounds of the formula (V) are then, if required, converted into compounds of the formula (V)'

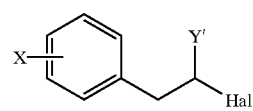

(V)' in which
X and Hal are as defined under formula (I) and
Y' represents COOH, COCl or COBr,
and a compound of the formula (V)' is cyclized to a 2-halogenoindan-1-one of the formula (I).
In the formulae,
X preferably represents chlorine, bromine or trifluoromethyl,
Hal preferably represents chlorine,
Y preferably represents COOH, $COOC_1$–$C_4$-alkyl or CN and
Y' preferably represents COOH or COCl.
The reaction of anilines of the formula (II) to diazonium salts of the formula (III) can be carried out according to generally known methods for preparing diazonium salts.

The aniline can, for example, be dissolved in water together with hydrochloric or hydrobromic acid, and this solution is initially admixed, for example, with sodium chloride or bromide, more hydrochloric or hydrobromic acid and water, and, at a controlled temperature (for example from −5 to +15° C.), a solution of sodium nitrite in water is metered in. This gives, if appropriate after a period of additional stirring, an aqueous solution of a diazonium salt of the formula (III) which can be reacted as such with an acrylic compound of the formula (IV).

The reaction of the solution of the diazonium salt of the formula (III) with an acrylic compound of the formula (IV) can be carried out, for example, by dissolving the acrylic compound of the formula (IV) in a water-miscible organic solvent, for example acetone, and adding the solution of the diazonium salt to this solution (careful: evolution of gas!). The temperature here can be, for example, from 10 to 60° C. It is advantageous to employ an excess of the acrylic compound, for example from 105 to 150% by weight of the amount which is theoretically required. Furthermore, it is advantageous to carry out the reaction in the presence of copper(II) and/or iron(II) salts. To this end, for example, an aqueous solution of copper (II) chloride or bromide or iron(II) chloride can be added to the solution of the acrylic compound of the formula (IV). Per 100 g of acrylic compound of the formula (IV), it is possible to employ, for example, from 2 to 50 g of copper(II) and/or iron(II) salts. This amount is preferably from 3 to 20 g.

If required after a period of additional stirring, the reaction mixture can be worked up, for example, by distilling off the solvent and, if appropriate, any excess acrylic compound which may still be present and admixing the residue with water and then with a water-immiscible solvent, such as diethyl ether, chloroform or toluene. After separation, the compound of the formula (V) produced can be isolated from the organic phase, if appropriate after washing with water, by stripping off the solvent and any acrylic compound of the formula (IV) which may still be present. If desired, the compound of the formula (V) can be purified further, for example by crystallization.

If Y in the compound of the formula (V) present represents $COOC_1$–$C_6$-alkyl or CN, it is now first of all necessary to carry out a conversion into a compound of the formula (V)' in which Y' represents COOH, COCl or COBr. It is possible, for example, to obtain from compounds of the formula (V) compounds of the formula (V)' where Y'=COOH by ester hydrolysis, which is known per se. The latter compounds can, if desired, be converted into compounds of the formula (V)' where Y'=COCl or COBr by using, for example, an acid halide preparation which is known per se, for example a reaction of a compound of the formula (V) or (V)' where Y or Y'=COOH with thionyl chloride, phosphorus trichloride or phosphorus tribromide.

For the cyclization step according to the invention for converting a compound of the formula (V)' to a 2-halogenoindan-1-one, it is possible to use two variants.

1st variant

A compound of the formula (V)' where Y'=COOH is admixed with a condensing agent and heated. Suitable condensing agents are, for example, polyphosphoric acid, mixtures of polyphosphoric acid and phosphorus pentoxide, methanesulphonic acid, mixtures of methanesulphonic acid and phosphorus pentoxide, sulphuric acid, hydrofluoric acid or trifluoromethanesulphonic acid. The condensing agent is generally employed in excess, for example from 500 to 5000 g, preferably from 600 to 4000 g, of condensing agent per 100 g of the compound of the formula (V)'. The reaction temperature can be, for example, from 25 to 120° C., preferably from 30 to 110° C. From the reaction mixture which is present after the condensation, it is possible to obtain the 2-halogenoindan-1-one prepared, for example by cooling the reaction mixture, pouring it into ice-water, taking up the organic components in a water-immiscible solvent, for example diethyl ether, chloroform or toluene, drying the organic phase and removing the solvent.

2nd variant

A compound of the formula (V)' where Y'=COCl or COBr is admixed with a Friedel-Crafts catalyst and heated. Suitable Friedel-Crafts catalysts are, for example, aluminium trichloride, iron trichloride, zinc chloride, aluminium bromide, mixtures thereof and melts of aluminium trichloride/sodium chloride. The Friedel-Crafts catalysts can be employed, for example, suspended in an inert solvent and in amounts of, for example, from 0.9 to 1.3 mol, based on one mole of the compound of the formula (V)' where Y'=COCl or COBr. Suitable reaction temperatures are, for example, those of from 50 to 100° C. Work-up of the reaction mixture can be carried out as for the 1st variant.

The process according to the invention gives, selectively and in good yields, indan-1-ones which are halogenated in the 2 position These can, if required after further finctionalizations, be used as starting material for applications such as those mentioned, for example, in WO 95/29171 and DE-A 26 40 358.

It is surprising that the reversal of the known synthesis route for 2-halogenoindan-1-ones, i.e. carrying out the synthesis, according to the invention, of the indanone skeleton as the last process step, is so much more favourable than the halogenation of indanones, in particular since the synthesis of the indanone skeleton as the last process step in the preparation of 5-halogenoindan-1-ones is not particularly advantageous.

The invention is further described in the following illustrative examples in which all parts and percentages are by weight unless otherwise indicated.

EXAMPLES

Example 1

129 g of 3-chloroaniline were dissolved in a hot solution of 480 ml of water and 108 ml of concentrated aqueous hydrochloric acid, and the mixture was then cooled to room temperature (→ solution I). 68.4 g of sodium nitrite were then dissolved in 104 ml of water (→ solution II). Solution I was then admixed with 103 g of sodium chloride, 140 ml of concentrated aqueous hydrochloric acid and 108 ml of water, and the solution was cooled to 0°C. Solution II was then added dropwise under the surface of solution I such that the temperature did not exceed +5° C. After the addition had ended, stirring was continued for 30 minutes.

In a further reaction vessel, 1600 ml of acetone and 387 g of acrylic acid were mixed and heated to 60° C., and a solution of 20 g of copper(II) chloride in 50 ml of water was added.

Over a period of 1 hour, the combined solutions I+II were added to the acetonic acrylic acid solution, which was at 55–60° C. (evolution of gas!). After the addition had ended, the mixture was heated under reflux for another 30 minutes, and the acetone and excess acrylic acid were then distilled off. 560 ml of water and 700 ml of toluene were added to the remaining solution, the organic phase was separated off and washed with 2×600 ml of water and the toluene and the remaining acrylic acid were then distilled off.

This gave 162.4 g of 2-chloro-3-(3-chlorophenyl)-propionic acid. If desired, the product can be purified further by crystallization.

Example 2

The procedure of Example 1 was repeated, but 4-chloroaniline was used instead of 3-chloroaniline. This gave 2-chloro-3-(4-chlorophenyl)-propionic acid in a yield of 74%.

Example 3

11 g of 2-chloro-3-(4-chlorophenyl)-propionic acid were taken up in 140 g of polyphosphoric acid, and the mixture was stirred at 100° C. for 90 minutes. The reaction mixture was then cooled to 55° C. and the material was introduced into 500 g of ice-water. The organic components were extracted with chloroform, the organic phase was then dried and the chloroform was distilled off. This gave 9.5 g of 2,6-dichloroindan-1-one.

Example 4

The procedure of Example 3 was repeated, but using 2-chloro-3-(3-chlorophenyl)-propionic acid as starting material for the cyclization. This gave a total yield of dichloroindan-1-ones of 78%. The 2,5-dichloroindan-1-one content was 75% by weight, the 2,7-dichloroindan-1-one content was 25% by weight.

Example 5

219 g of 2-chloro-3-(4-chlorophenyl)-propionic acid were initially charged and heated to 70° C. 226 g of thionyl chloride were then added (evolution of gas!) and the mixture was kept at reflux until the evolution of gas had ceased. Subsequently, first the excess thionyl chloride and then, under reduced pressure, the 2-chloro-3-(4-chlorophenyl)-propionyl chloride (b.p., at from 7 to 8 mbar, 132 to 135° C.) were distilled off (226 g of product).

The acid chloride obtained in this manner was then cyclized. To this end, 6.7 g of anhydrous aluminium chloride were suspended in 75 ml of a benzine fraction which boiled at from 60 to 95° C., this mixture was heated to 60° C. and a solution of 11.9 g of the acid chloride in 50 ml of the benzine mentioned was added dropwise. The mixture was subsequently stirred at 60° C. for 2 hours. The reaction mixture was poured onto ice to which a little hydrochloric acid had been added. The organic components were subsequently extracted with diethyl ether and the ether was distilled off, giving the desired 2,6-dichloroindan-1-one (9.8 g).

Example 6

The procedure of Example 5 was repeated, but using 2-chloro-3-(3-chlorophenyl)-propionic acid instead of 2-chlor-3-(4-chlorophenyl)-propionic acid. This gave dichloroindan-1-ones in a total yield of 96.4%. The 2,5-dichloroindan-1-one content was 85% by weight, the 2,7-dichloroindan-1-one content was 15% by weight.

Although the present invention has been described in detail with reference to certain preferred versions thereof, other variations are possible. Therefore, the spirit and scope of the appended claims should not be limited to the description of the versions contained therein.

What is claimed is:

1. Process for preparing 2-halogenoindan-1-ones of the formula (I)

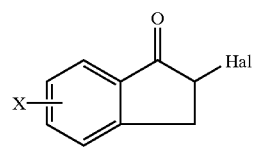

wherein x represents a member selected from the group consisting of hydrogen, fluorine, chlorine, bromine, methyl, trifluoromethyl, methoxy and Hal represents chlorine or bromine, wherein an aniline of the formula

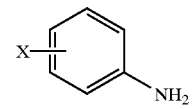

wherein

X is as defined under formula (I)

is converted into the corresponding diazonium salt of the formula (III)

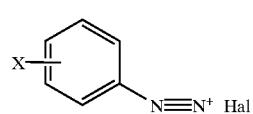

wherein

X and Hal are as defined under formula (I), and this salt is reacted with an acrylic compound of the formula (IV)

wherein

Y represents COR wherein R is OH, Cl, Br, $OC_1$–$C_4$-alkyl or CN, thus giving a compound of the formula (V)

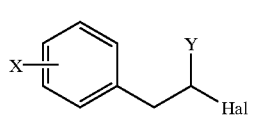

wherein

X and Hal are as defined under formula (I) and

Y is as defined under formula (IV), and compounds of the formula (V) are then converted into compounds of the formula (V)'

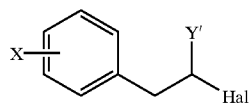 (V)' wherein

X and Hal are as defined under formula (I) and

Y' represents COOH, COCl or COBr, and a compound of the formula (V)' is cyclized to a 2-halogenoindan-1-one of the formula (I).

2. Process according to claim 1, wherein the reaction of the diazonium salt of the formula (III) with an acrylic compound of the formula (IV) is carried out by initially charging the acrylic compound of the formula (IV) in a water-miscible organic solvent and adding the solution of the diazonium salt to this solution, and the reaction temperature is maintained at from about 10 to about 60° C. and an excess of the acrylic compound is employed.

3. Process according to claim 1, wherein the reaction of the diazonium salt of the formula (III) with an acrylic compound of the formula (IV) is carried out in the presence of copper(II) and/or iron(II) salts.

4. Process according to claim 1, wherein if a compound of the formula (V)' wherein Y' is COOH is employed, the cyclization step is carried out by admixing with a condensing agent and at a temperature of from about 25 to about 120° C.

5. Process according to claim 1, wherein a compound of the formula (V)' wherein Y' is COCl or COBr is employed, and the cyclization step is carried out by adding a Friedel-Crafts catalyst and at a reaction temperature of from about 50 to about 100° C.

* * * * *